(12) United States Patent
Yang (10) Patent No.: US 8,449,506 B2
(45) Date of Patent: May 28, 2013

(54) AUTOMATIC FEEDING/PHLEGM EXTRACTOR DEVICE

(76) Inventor: Chang Ming Yang, Miaoli (TW)

( * ) Notice: Subject to any disclaimer, the term of this patent is extended or adjusted under 35 U.S.C. 154(b) by 1501 days.

(21) Appl. No.: 11/989,046

(22) PCT Filed: Jul. 20, 2005

(86) PCT No.: PCT/CN2005/001081
§ 371 (c)(1),
(2), (4) Date: Jan. 18, 2008

(87) PCT Pub. No.: WO2007/009294
PCT Pub. Date: Jan. 25, 2007

(65) Prior Publication Data
US 2009/0112160 A1   Apr. 30, 2009

(51) Int. Cl.
*A61M 5/00* (2006.01)
(52) U.S. Cl.
USPC ........................................................ 604/257
(58) Field of Classification Search
USPC ................ 604/113, 146, 147, 181, 257, 910
See application file for complete search history.

(56) References Cited

U.S. PATENT DOCUMENTS

| | | | | |
|---|---|---|---|---|
| 2,254,833 | A * | 9/1941 | Ashkenaz | 604/245 |
| 3,640,277 | A * | 2/1972 | Adelberg | 604/141 |
| 4,613,327 | A * | 9/1986 | Tegrarian et al. | 604/141 |
| 5,195,961 | A * | 3/1993 | Takahashi et al. | 604/35 |
| 5,294,022 | A * | 3/1994 | Earle | 222/56 |
| 5,428,993 | A * | 7/1995 | Kobashi | 73/149 |
| 6,048,086 | A * | 4/2000 | Valerino, Sr. | 706/10 |
| 6,061,608 | A * | 5/2000 | Moldavsky | 700/240 |
| 6,280,408 | B1 * | 8/2001 | Sipin | 604/65 |
| 6,447,472 | B1 * | 9/2002 | Moss | 604/27 |
| 6,537,244 | B2 * | 3/2003 | Paukovits et al. | 604/65 |
| 7,048,727 | B1 * | 5/2006 | Moss | 604/508 |
| 2006/0119484 | A1 * | 6/2006 | Chishima et al. | 340/612 |
| 2006/0129127 | A1 * | 6/2006 | Ruth et al. | 604/514 |
| 2007/0060898 | A1 * | 3/2007 | Shaughnessy et al. | 604/284 |
| 2008/0039778 | A1 * | 2/2008 | Goldie et al. | 604/67 |
| 2009/0236361 | A1 * | 9/2009 | Doelman et al. | 222/1 |
| 2010/0108717 | A1 * | 5/2010 | Szymanski | 222/100 |

\* cited by examiner

*Primary Examiner* — Victoria P. Shumate
*Assistant Examiner* — Diva K Chander
(74) *Attorney, Agent, or Firm* — Osha Liang LLP (57) ABSTRACT

An automatic feeding/sputum suction device, which mainly comprises a feeding syringe or sputum suction device, an air pump, a liquid food replenishing drum or oxygen/water supply device, three-way control valve, feeding duct or sputum suction duct, controller and detector strap, wherein the three-way control valve is connected with liquid food replenishing drum (oxygen/water supply device), feeding syringe (sputum suction device) and feeding duct (sputum suction duct).

19 Claims, 6 Drawing Sheets

AUTOMATIC FEEDING/PHLEGM EXTRACTOR DEVICE

BACKGROUND OF THE PRESENT INVENTION

1. Field of Invention

The present invention relates to an automatic feeding/sputum suction device and particularly, it relates to an automatic feeding/sputum suction device that can detect whether patients are experiencing any discomfort in the process of feeding and sputum suction.

2. Description of Related Arts

For many types of nervous system diseases, throat muscles may gradually discontinue normal function in response to aggravation of diseases, thus causing such symptoms as difficulty in swallowing, suffocation, choking, aphonia and difficulty in breathing. In case of difficulty in swallowing, patients eat less and cannot take in sufficient nutriments. Now, it is required to use feeding duct (Nasogastric duct is inserted in through nasal cavity and goes to stomach through esophagus; or stomach duct is inserted into stomach directly through abdomen via operation) to feed liquid food. In most cases, feeding duct can help prevent diseases and extend life. For such diseases as ALS (amyotrophic lateral sclerosis), feeding duct may form part of normal treatment (In later period of disease, swallowing function may be affected).

In addition to application for patients with difficulty in swallowing, feeding duct is also applicable to patients after operation in oral cavity, throat, esophagus and trachea and those with unconsciousness, severe melancholy or fastidium. Before use, medical staff pours liquid food (such as milk and juice) into feeding syringe and raises feeding syringe about 30-45 cm to let liquid food to flow in slowly by gravity. However, only 250 cc-350 cc can be fed per time and this process lasts 15-20 minutes. In addition, patients may sometimes experience nausea, vomiting, diarrhea, sweating, spasm and faster heartbeat in the process of feeding. In this case, feeding must be discontinued immediately and medical staff has to deal with this situation. Therefore, medical staff has to watch for any discomfort of patients while feeding. As a result, medical negligence tends to occur in this process.

In addition, if patients have had tracheotomy, windpipe is often inserted to suction sputum or feed food. In the process of sputum suction or feeding, food tends to flow in through windpipe and lead to inhalation pneumonia. Therefore, it is necessary to suck out sputum.

It can be concluded that prior art has a full range of defects and needs improvement.

SUMMARY OF THE PRESENT INVENTION

One objective of the present invention is to provide an automatic feeding/sputum suction device easy for medical staff to operate.

Another objective of the present invention is to provide an automatic feeding/sputum suction device that can detect whether patients are experiencing any discomfort in the process of feeding and sputum suction.

The automatic feeding/sputum suction device of the present invention comprises:

a feeding syringe;

a liquid food replenishing drum, which further comprises a water storage tank and a liquid food storage tank;

a three-way valve, which is connected with liquid food replenishing drum, feeding syringe and feeding duct;

a feeding duct;

a controller, which may control the opening and closing of each channels way of the three-way valve;

a detector strap, which is attached to the body of patients as a breath detector; and an air pump, which is connected with controller.

Still further objects and advantages will become apparent from a consideration of the ensuing description and drawings.

These and other objectives, features, and advantages of the present invention will become apparent from the following detailed description, the accompanying drawings, and the appended claims.

BRIEF DESCRIPTION OF THE DRAWINGS

To further understand the technical contents and functions of the present invention, please refer to detailed description of preferred embodiments and drawings. Relevant drawings are attached below.

Designations for key components in the enclosed drawings: 1. Liquid food replenishing drum; 2. Switch; 3. Three-way valve; 4. Oxygen/water supply device; 5. Feeding syringe; 51. Syringe adaptor; 6. Piston; 7. Infrared detector; 8. Ultrasonic detector; 9. Air tank; 91. Air leading needle; 92. Pine hole.

DETAILED DESCRIPTION OF THE PREFERRED EMBODIMENT

Figure 1:
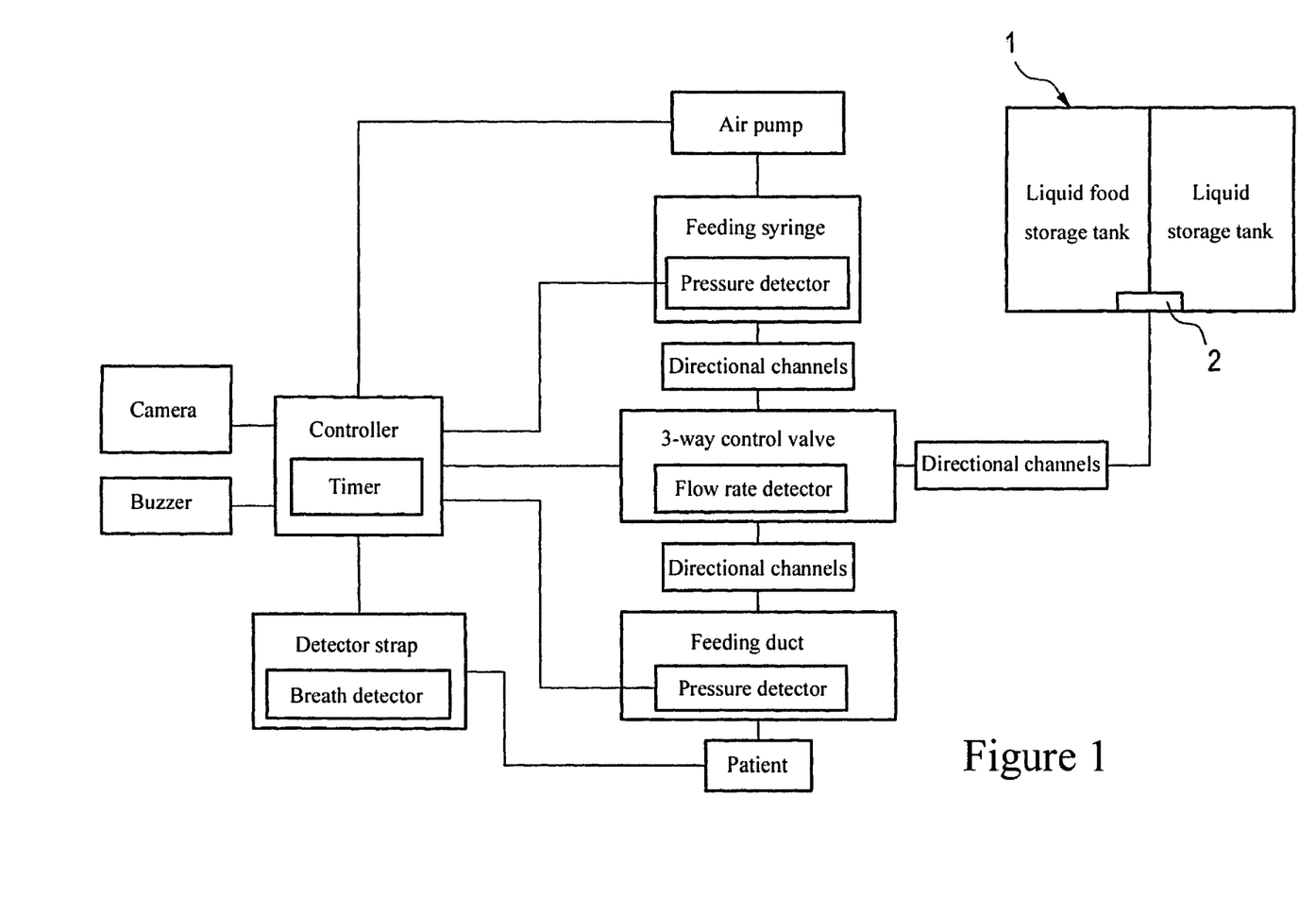
FIG. 1 is the block diagram of the automatic feeding device in the present invention.
Figure 2:
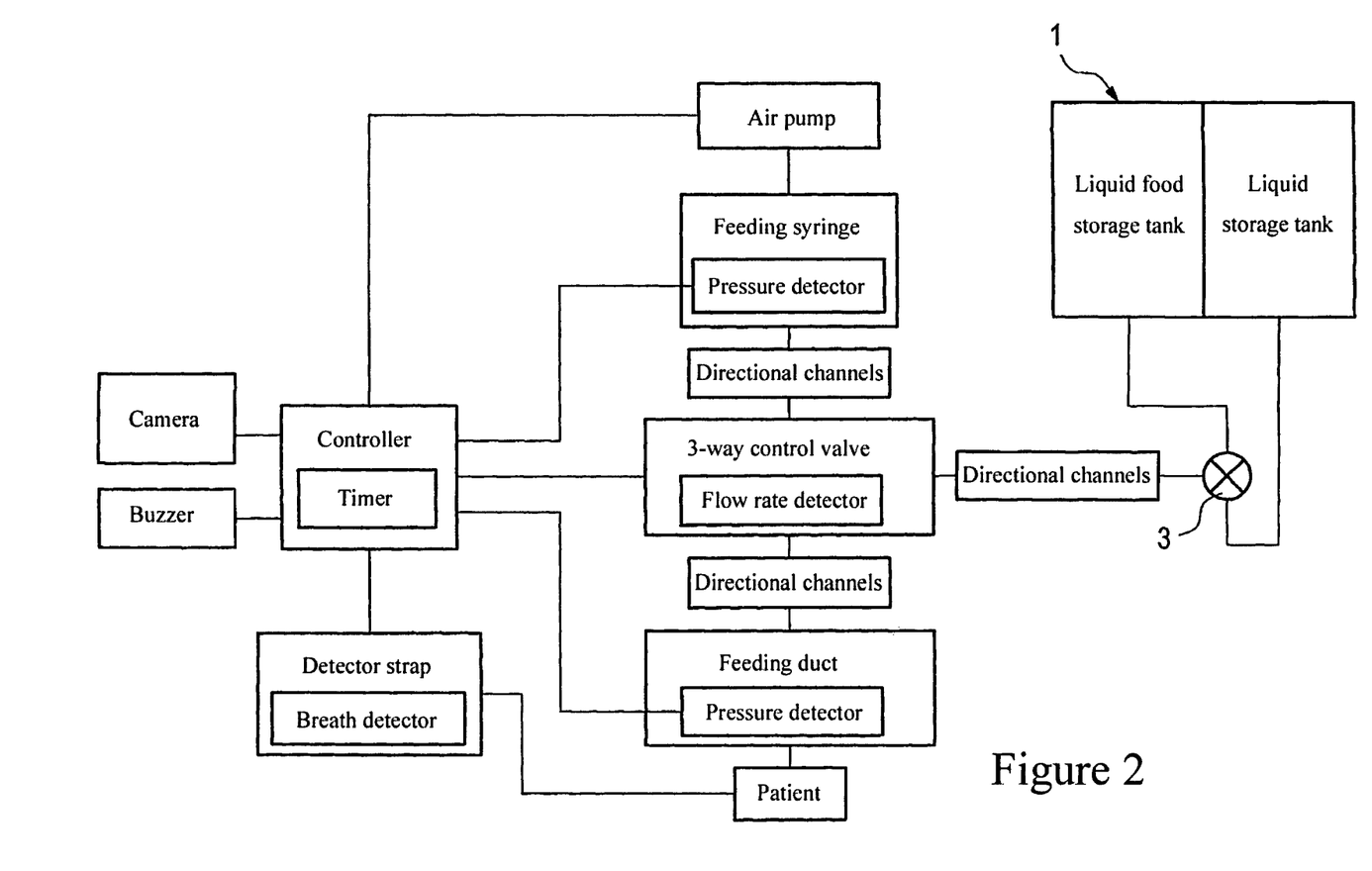
FIG. 2 is the block diagram of the first embodiment of the automatic feeding device in the present invention.
Figure 3:
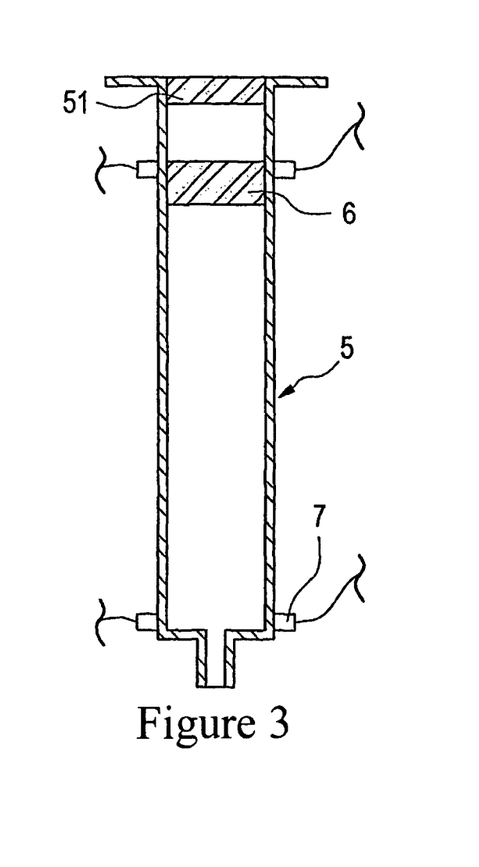
FIG. 3 is the side view of the first embodiment of the feeding syringe.

As shown in FIGS. 1, 2 and 3, the automatic feeding device in the present invention mainly comprises:

A feeding syringe 5, wherein a piston 6 is provided in feeding syringe 5 and feeding syringe 5 is connected with air pump through a syringe adaptor 51.

A liquid food replenishing drum 1, wherein a water storage tank and a liquid food storage tank are provided, and a heating or a thermal insulation device is set in liquid food replenishing drum 1 and the liquid food replenishing drum 1 is connected with a three-way control valve 3 and a feeding syringe 5.

A three-way control valve 3, which is connected with liquid food replenishing drum 1, feeding syringe 5 and feeding duct by its three-way channels.

A feeding duct, which is inserted into stomach through mouth or nose or directly into stomach intestine.

A controller, which may control the opening and closing of each channel of the three-way valve.

A detector strap, wherein the detector strap is attached to the body of patients; the detector strap comprises two resilient sides; the two resilient sides are interconnected and provided with a contact switch serving as breath detector, and An air pump, which is connected with controller.

Operating procedures for the automatic feeding device of the present invention:

Step 1. Use the controller to open or manually open the directional channels of the three-way control valve which is connected with feeding syringe 5 and liquid food replenishing drum 1.

Step 2. Use switch 2 or three-way valve 3 to open water storage tank of liquid food replenishing drum 1.

Step 3. Use the air pump to propel piston 6 in feeding syringe 5 to pump 20 cc-30 cc warm water from water storage tank to feeding syringe 5.

Step 4. Close water storage tank of liquid food replenishing drum 1.

Step 5. Use the controller to close or manually close the directional channel of the three-way valve which is connected with liquid food replenishing drum 1.

Step 6. Open the directional channels which is connected with feeding syringe 5 and feeding duct.

Step 7. Use the air pump to propel piston 6 in feeding syringe 5 to pump 20 cc-30 cc warm water from feeding duct to patient's stomach.

Step 8. Use the controller to close or manually close the directional channels of the three-way valve which is connected with feeding duct.

Step 9. Use the controller to open or manually open the directional channels of the three-way valve which is connected with the feeding syringe 5 and the liquid food replenishing drum 1.

Step 10. Use switch 2 or three-way valve 3 to open the liquid food storage tank of liquid food replenishing drum 1.

Step 11. Use air pump to propel piston 6 in feeding syringe 5 to pump proper amount of liquid food into feeding syringe 5.

Step 12. Close the liquid food storage tank of liquid food replenishing drum 1.

Step 13. Use the controller to close or manually close the directional channel of the three-way valve which is connected with liquid food replenishing drum 1.

Step 14. Open the directional channel, which is connected with feeding syringe 5 and feeding duct.

Step 15. Use the air pump to propel piston 6 in feeding syringe 5 to pump proper liquid food from feeding duct to patient's stomach.

Step 16. Use the controller to close or manually close the directional channel of the three-way valve, which is connected with feeding duct.

Step 17. Use the controller to open or manually open the directional channel of the three-way valve which is connected with feeding syringe 5 and liquid food replenishing drum 1.

Step 18. Repeats steps 2-7; use warm water to flush remaining liquid food in feeding duct into patient's stomach to prevent residual food from sticking on the wall of feeding duct.

In the automatic feeding device of the present invention, an external or built-in buzzer or alarm device may be provided in the controller; a pressure detector may be provided in feeding syringe 5 and feeding duct; the pressure detector in feeding syringe 5 is used to detect the remaining amount of liquid food or warm water in feeding syringe 5 (When detected pressure suddenly turns low, it indicates liquid food or warm water in feeding syringe 5 is exhausted; When detected pressure suddenly turns high, it indicates feeding duct is blocked, making it impossible for liquid food or warm water in feeding syringe 5 cannot be fed into patient's stomach). In addition, pressure detector in feeding duct may detect vomiting of patient in the feeding process (When detected pressure suddenly turns high, it indicates the patient is vomiting, thus causing food in stomach to flow back into feeding duct and causing pressure rise in feeding duct). When pressure detector in feeding syringe 5 and feeding duct detects any change in pressure, the controller will cause buzzer or alarm device to give off sound or lighting signal, requesting medical staff to deal with the situation. Besides, an infrared detector may be provided between the three-way control valve and liquid food storage tank. When the air pump is pumping liquid food to the feeding syringe, if no liquid food or water is available in the liquid food storage tank, the infrared detector will send signal to the controller and the controller will cause buzzer or alarm device to give off sound or lighting signal, requesting medical staff to stop feeding and replenish liquid food storage tank.

When the automatic feeding device of the present invention is in feeding process, the detector strap is attached on patient's body (or on patient's chest, arm or nose depending on how to detect). Patient's inhalation enables the detector strap to expand outward such that the two contact switches in the detector strap contact each other to detect the patient's breathing frequency. When it detects the patient is breathing too fast, which means the patient is experiencing some discomfort in feeding process, the controller causes buzzer or alarm device to give off sound or lighting signal, requesting medical staff to deal with the situation. In addition, the detector strap may be provided with an acceleration detector or a cardiogram detector or an electromyogram detector or a pressure detector in place of breath detector, or it may be provided with a built-in microphone to monitor patient's breath and heartbeat. Furthermore, the detector strap may also be provided with humidity detector to detect patient's sweating degree. Also, the controller may be connected with a blood oxygen concentration detector attachable behind patient's ears or on fingers to detect the degree of anoxia. If the pressure detector is provided on the detector strap attached on arm, it can detect pulse or heartbeat rate.

In the automatic feeding device of the present invention, the feeding duct may be provided with a temperature detector connected with the controller. The temperature detector may detect the temperature of liquid food or water that flow through feeding duct and work with the controller to set upper and lower temperature limit. When the temperature detector detects the temperature of liquid food or water exceeds upper or lower limit, the controller may stop feeding operation and cause buzzer or alarm device to give off sound or lighting signal, requesting medical staff to deal with the situation.

In the automatic feeding device of the present invention, the detector strap may be substituted by a nasal sucker hung on patient's nose. In addition, a pressure detector may be provided behind the nasal sucker, which calculates patient's breathing frequency based on pressure change in response to patient's inhalation and exhalation through nasal sucker. Furthermore, the nasal sucker may be connected with an oxygen supply device to supply oxygen to patient where necessary.

In the automatic feeding device of the present invention, the liquid food replenishing drum may be provided with a volume gauge or weight detector to detect the amount of food fed each time. The three-way control valve may be provided with a flow rate detector which may detect flow rate using fine cord, light reflection, flow meter or according to the principle of PV=NRT for positive or negative pressure. Moreover, a timer can be provided on the controller to observe feeding speed and time. The controller can be connected with a camera with wire or wireless to record feeding time, feeding volume, patient name, side effect (if any), medical staff name and chest up/down movement in response to patient's breathing and thus detect patient's breathing frequency.

In the automatic feeding device of the present invention, a feeding bottle may be provided at the end of the feeding duct for feeding infants or animals. Moreover, a pipe extends outward at the front of the feeding bottle and membrane is provided in the pipe for ventilation to balance pressure inside and outside the feeding bottle.

Figure 3A:
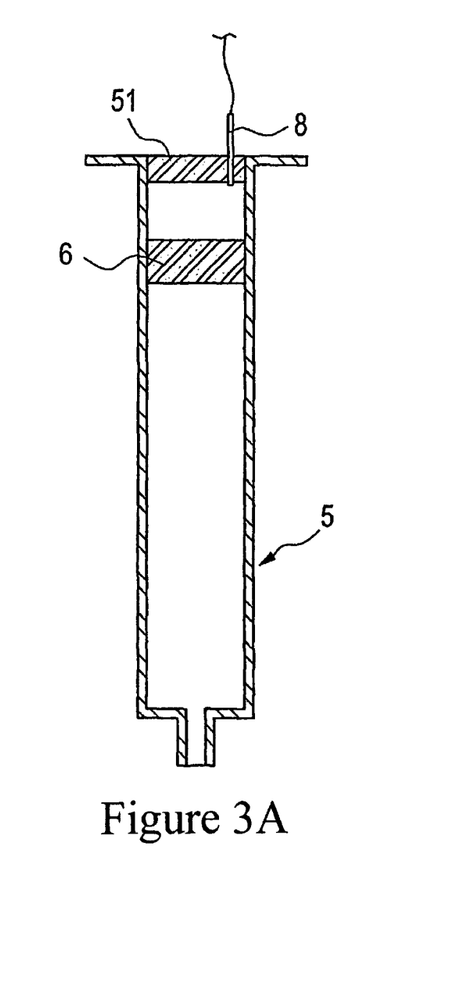
FIG. 3A is the side view of the second embodiment of the feeding syringe.

In the automatic feeding device of the present invention as shown in FIGS. 3 and 3A, the infrared detector 7 may be provided on the front and rear pipe wall of the feeding syringe 5 and connected with the controller to detect the position of piston 6 in the feeding syringe 5. When the infrared detector 7 detects piston 6 reaches the front end of the feeding syringe 5, it indicates all warm water or liquid food in the feeding syringe 5 has been fed into patient's stomach. Now, the controller causes air pump to pump liquid food into feeding syringe 5. When piston 6 reaches the position of infrared detector 7 at the rear end of the feeding syringe 5 (i.e., reaching preset feeding volume per time), the controller causes air pump to stop pumping. Also, the automatic feeding device of the present invention can be provided with ultrasonic detector 8 on the syringe adaptor to detect the position of piston 6.

Figure 4:
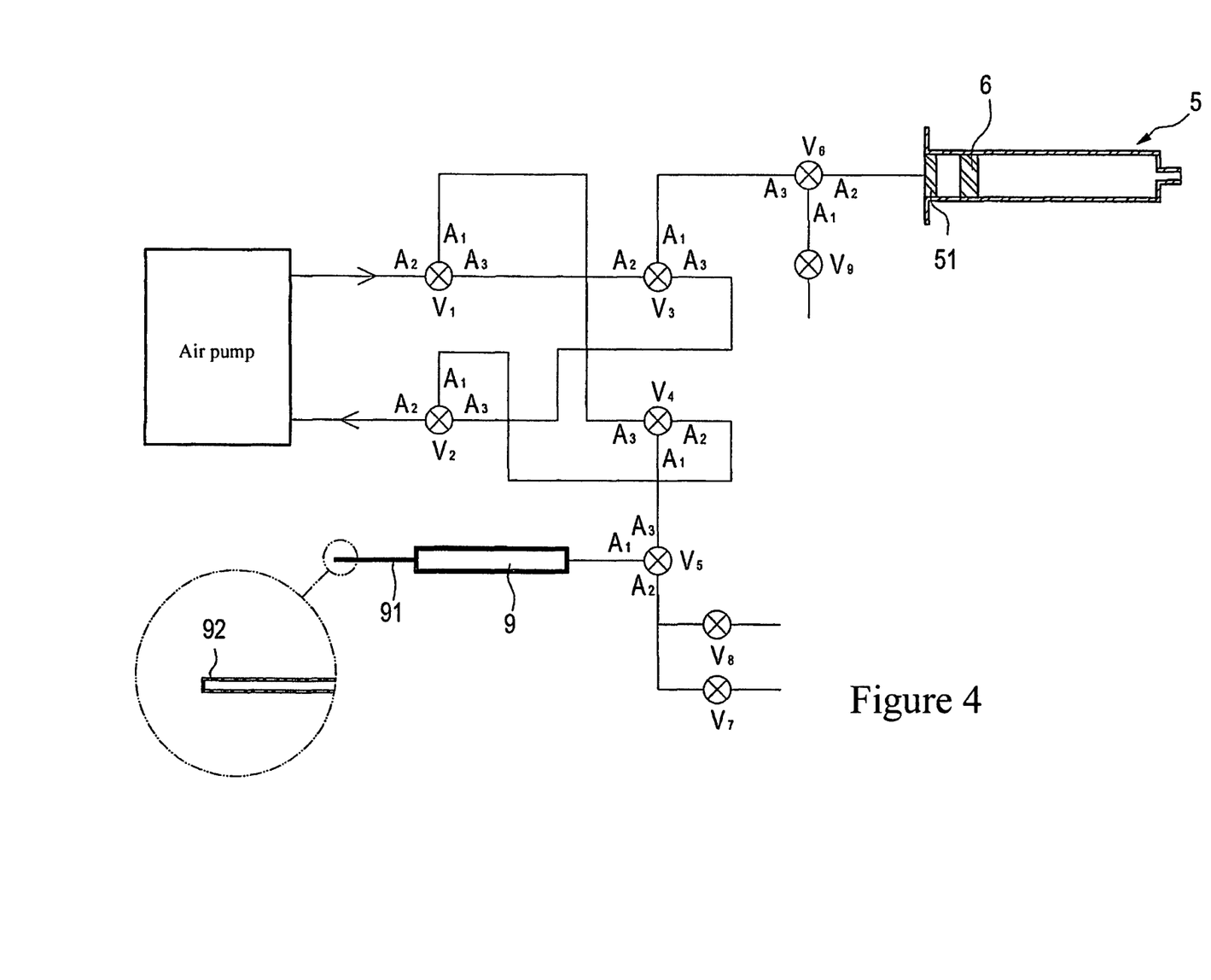
FIG. 4 is the block diagram of the control module.

In the automatic feeding device of the present invention as shown in FIGS. 1 and 4, the air pump propels piston 6 in feeding syringe 5 to pump warm water or liquid food into patient's stomach. To avoid causing discomfort to patient due to disruption of piston 6 in the process of propelling, a controller and an air tank 9 are provided between feeding syringe 5 and air pump in the automatic feeding device of the present invention, wherein the a controller—comprises three-way valve V1, three-way valve V2, three-way valve V3, three-way valve V4, three-way valve V5, three-way valve V6, leaking valve V7, leaking valve V8 and leaking valve V9; on both sides of each three-way valve are directional channels A2 and A3 while directional channel A1 is provided between channels A2 and A3; leaking valves V7 and V9 are for air inlet while leaking valve V8 is for air outlet. leaking valves V8 and V9 are interlinked; directional channel A2 of three-way valve V1 is connected with air outlet of air pump; directional channel A3 of three-way valve V1 is connected with directional channel A2 of three-way valve V3; directional channel A1 of three-way valve V1 is connected with directional channel A3 of three-way valve V4; directional channel A2 of three-way valve V2 is connected with air inlet of air pump; directional channel A1 of three-way valve V2 is connected with directional channel A2 of three-way valve V4; directional channel A3 of three-way valve V2 is connected with directional channel A3 of three-way valve V3; directional channel A1 of three-way valve V3 is connected with directional channel A3 of three-way valve V6; directional channel A1 of three-way valve V4 is connected with directional channel A3 of three-way valve V5; directional channel A1 of three-way valve V6 is connected with air tank 9; directional channel A2 of three-way valve V5 is connected with leaking valves V7 and V8; directional channel A1 of three-way valve V6 is connected with leaking valve V9; directional channel A2 of three-way valve V6 is connected with feeding syringe 5; in addition, one end of air tank 9 is connected with directional channel A1 of three-way directional V5 while the other end has an air leading needle 91 with pine hole 92. Operating procedures are as follows:

Step 1. When air pump is taking in air, close the directional channel A2 of three-way valve V5, directional channel A3 of three-way valve V4 and directional channel A3 of three-way valve V2.

Step 2. Air pump pumps air from air tank 9.

Step 3. When air pump is pumping out air, close the directional channel A1 of three-way valve V1, directional channel A3 of three-way valve V3 and directional channel A1 of three-way valve V6.

Step 4. The action of air pump pumping air from air tank 9 is used as propelling force to propel piston 6 in feeding syringe 5;

Step 5. Repeat step 1;

Step 6. Air pump keeps on pumping air via pine hole 92 in air leading needle 91;

Step 7. Repeat step 3.

Step 8. The action of air pump pumping air through pine hole 92 in air leading needle is used as propelling force to propel piston 6 in feeding syringe 5.

In the above process, air pump uses air in air tank 9 as initial force to propel piston 6 in feeding syringe 5. Since piston 6 contacts the wall of feeding syringe 5, it has to propel piston 6 with great force at first. Once it begins to propel piston 6, less force is needed to propel piston 6. Therefore, continuous action of pine hole 92 in air leading needle to pump air can be used as propelling force to propel piston 6 and thus prevent piston 6 from stopping because initial force piston 6 is equal to its maintaining force when air pump is propelling piston 6. Moreover, since leaking valves V8 and V9 are interlinked, leaking valve V8 is open while leaking valve V9 is open and vice versa. Therefore, when leaking valve V9 is open to take in air, it propels piston 6 in feeding syringe 5 forward and when leaking valve V8 is open to release air, it pulls piston 6 in feeding syringe 5 backward to engage piston 6 with the wall of feeding syringe 5. Furthermore, leaking valve V7 replenishes air to air tank 9 immediately after feeding is completed to facilitate next feeding process.

Figure 5:
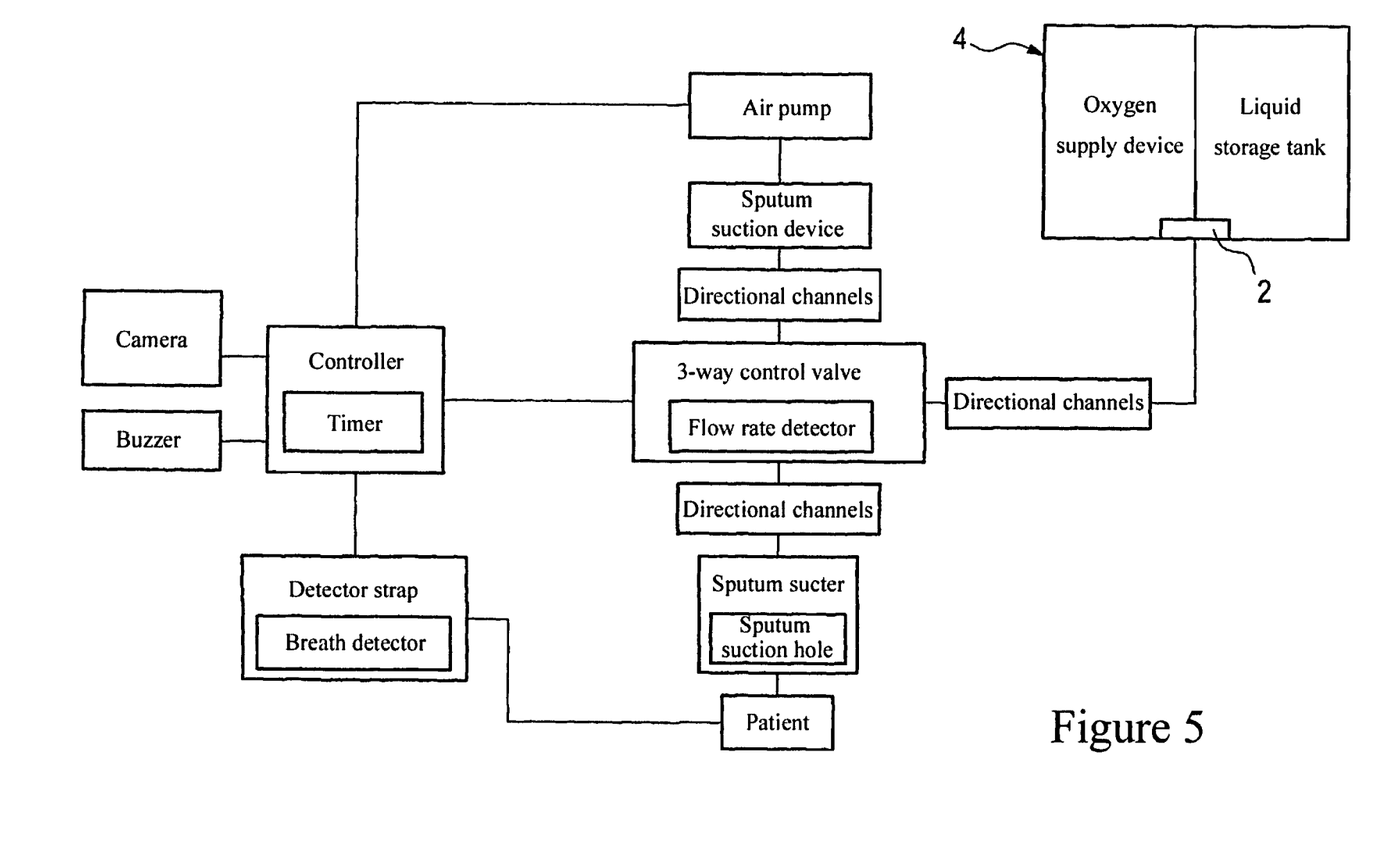
FIG. 5 is the block diagram of the automatic sputum suction device.
Figure 6:
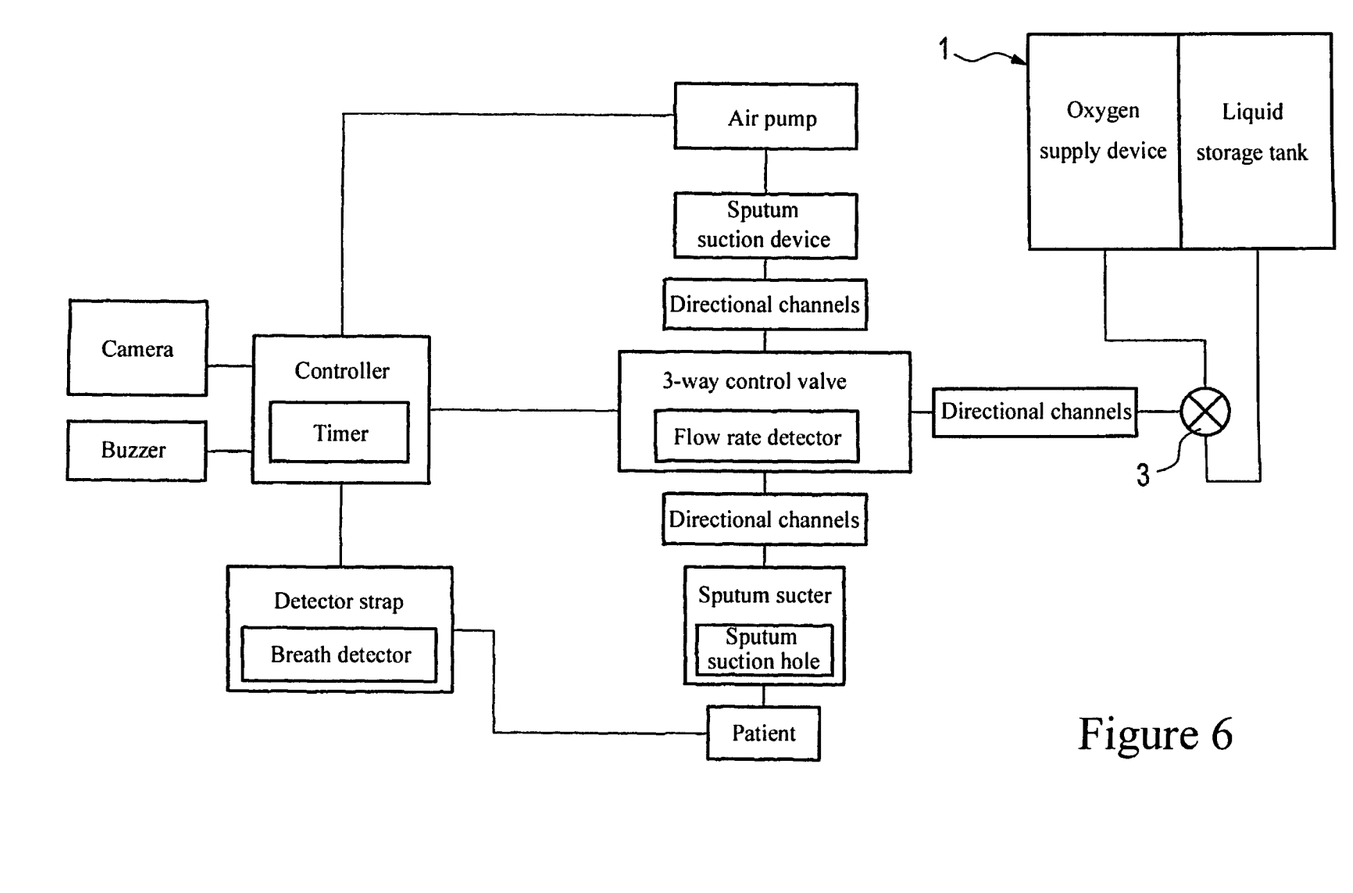
FIG. 6 is the block diagram of the first embodiment of the automatic sputum suction device.

As shown in FIGS. 5 and 6, the sputum suction device in the present invention comprises:

A sputum suction device, which is connected with an air pump;

An oxygen/water supply device 4, wherein an oxygen supply device and a liquid storage tank are provided in oxygen/water supply device 4; the oxygen supply device is an oxygen generator or an oxygen cylinder; and oxygen/water supply device 4 is connected with three-way control valve and sputum suction device;

A three-way control valve, which is connected with oxygen/water supply device 4, sputum suction device and sputum suction duct;

A sputum suction duct, wherein a plurality of sputum suction holes are arranged around the sputum duct;

A controller, which controls the opening and closing of the directional channels of three-way control valves and is provided with an external or built-in buzzer or alarm device;

A detector strap, which is attached to patient's body and comprises two resilient sides; the two resilient sides are interconnected and provided with a contact switch serving as breath detector;

An air pump, which is connected with controller.

Operating procedures of the automatic sputum suction device in the present invention are as follows:

Step 1. Insert sputum suction duct into patient's body where suction is required.

Step 2. Use a controller to open or manually open the directional channels of the three-way valve which is connected with oxygen/water supply device 4 and liquid sputum suction duct.

Step 3. Use switch 2 or three-way valve 3 to open oxygen supply device of oxygen/water supply device 4.

Step 4. Enable oxygen supply device to supply about one-minute oxygen to patients via sputum suction duct.

Step 5. Use switch 2 or three-way valve 3 to close oxygen supply device of oxygen/water supply device 4.

Step 6. Use a controller to open or manually open the directional channels of the three-way valve which is connected with sputum suction device and sputum suction duct.

Step 7. Start sputum suction device to enable sputum suction duct to suck sputum into sputum suction device via sputum suction holes.

Step 8. Shut off sputum suction device.

Step 9. Use a controller to open or manually open the directional channels of the three-way valve which is connected with oxygen/water supply device 4 and sputum suction duct.

Step 10. Use switch 2 or three-way valve 3 to open oxygen supply device of oxygen/water supply device 4 to supply oxygen to patient.

Step 11. Use switch 2 or three-way valve 3 to close oxygen supply device of oxygen/water supply device 4.

Step 12. Medical staff rotates sputum suction duct to enable sputum suction holes of sputum suction device to point towards other angles.

Step 13. Repeat steps 6-12 until sputum suction duct rotates 360° (i.e., sputum suction holes rotate 360° to suck sputum in every angle.

Step 14. Turn off sputum suction device.

Step 15. Pull sputum suction duct from patient.

After the automatic sputum suction device in the present invention completes sputum suction, it may use switch 2 or three-way valve 3 to open water storage tank of oxygen/water supply device 4 and switch three-way control valve to connect oxygen/water supply device 4 with sputum suction device or sputum suction duct. After that, air pump will pump water from water storage tank to flush sputum suction device and sputum suction duct. In addition, in the process of sputum suction, a detector strap is attached on patient's body. In response to patient's inhalation, the detector strap extends outward such that the two contacts in the detector strap contact each other to detect patient's breathing frequency. When it detects the patient is breathing too fast, which means the patient is experiencing faster heartbeat due to discomfort, the controller causes buzzer or alarm device to give off sound or lighting signal, requesting medical staff to deal with the situation. In addition, the detector strap may be provided with acceleration cardiogram detector or electromyogram detector or pressure detector in place of breath detector, or it may be provided with built-in microphone to monitor patient's breath and heartbeat. Furthermore, in the automatic sputum suction device of the present invention, an atomizer may be provided at the outlet of the oxygen supply device to meet the needs of patients who need to use atomized inhalants. If pressure detector is provided on detector strap attached on arm, it can detect pulse or heartbeat rate. Besides, an infrared detector may be provided between the three-way control valve and oxygen/water supply device 4. In the process of supplying oxygen to patient, if infrared detector detects there is no oxygen going through, it may send signal to controller and controller will cause buzzer or alarm device to give off sound or lighting signal, requesting medical staff to deal with the situation and stop sputum suction.

In the automatic sputum suction device of the present invention, the detector strap may also be provided with humidity detector to detect patient's sweating degree. Also, the controller may be connected with a blood oxygen concentration detector attachable behind patient's ears or on fingers to detect the degree of anoxia. The detector strap may be substituted by a nasal sucker hung on patient's nose. In addition, a pressure detector may be provided behind the nasal sucker, which calculates patient's breathing frequency based on pressure change in response to patient's inhalation and exhalation through nasal sucker. Furthermore, the nasal sucker may be connected with an oxygen supply device to supply oxygen to patient where necessary.

The above description is only one preferred embodiment of the present invention. This embodiment shall not limit the scope of the patent of the present invention. All similar embodiments or modifications that fall into the technical conception of the present invention shall be included in the scope of the present invention.

INDUSTRIAL APPLICATIONS

The automatic feeding/sputum suction device in the present invention is easy for medical staff to operate. In the process of feeding or sputum suction, it can accurately detect patient's discomfort. It can be extensively used in medical care and has extensive industrial applications.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. An automatic feeding device, which comprises:
   a pump to propel a liquid;
   a controller to control the pump;
   a feeding duct to convey the liquid; and
   a liquid supply device, which is provided with a volume gauge or weight detector to measure an amount of the liquid fed,
      wherein the liquid supply device is further provided with a heating or insulating device, or
      wherein an infrared detector is provided at the liquid supply device and connected to the controller to determine whether the liquid supply device is empty.

2. The device as recited in claim 1, wherein the liquid supply device is provided with a heating or insulating device.

3. The device, as recited in claim 1, wherein an infrared detector is provided at the liquid supply device and connected to the controller to determine whether the liquid supply device is empty.

4. An automatic feeding device, which comprises:
   a pump to propel a liquid;
   a controller to control the pump;
   a feeding duct to convey the liquid;
   a liquid supply device, which is provided with a volume gauge or weight detector to measure an amount of the liquid fed; and
   an air tank connected with the pump, wherein the air tank is connected to an air leaking needle having at least one pin hole.

5. An automatic feeding device, which comprises:
   a pump to propel a liquid;
   a controller to control the pump;
   a feeding duct to convey the liquid;
   a liquid supply device, which is provided with a volume gauge or weight detector to measure an amount of the liquid fed;
   a detector strap, which is adapted to attach to a patient, and wherein the detector strap comprises two resilient sides and the two resilient sides are interconnected and provided with a contact switch.

6. The device, as recited in claim 5, wherein the detector strap comprises a breath detector.

7. The device, as recited in claim 5, wherein the detector strap is provided with an acceleration detector, a cardiogram detector, an electromyogram detector, or a pressure detector.

8. The device, as recited in claim 5, wherein the detector strap is provided with a microphone.

9. The device, as recited in claim 5, wherein the detector strap is provided with a humidity detector.

10. The device, as recited in claim 5, wherein the detector strap is provided with a pressure detector attachable to an arm of a patient to detect a heartbeat rate.

11. An automatic feeding device, which comprises:
a pump to propel a liquid;
a controller to control the pump;
a feeding duct to convey the liquid; and
a liquid supply device, which is provided with a volume gauge or weight detector to measure an amount of the liquid fed,
wherein the controller is connected with a buzzer or alarm device, or
wherein the controller can be connected with a camera with wire or wirelessly.

12. The device, as recited in claim 11, wherein the controller is connected with a buzzer or alarm device.

13. The device, as recited in claim 11, wherein the controller can be connected with a camera with wire or wirelessly.

14. An automatic feeding device, which comprises:
a pump to propel a liquid;
a controller to control the pump;
a feeding duct to convey the liquid;
a liquid supply device, which is provided with a volume gauge or weight detector to measure an amount of the liquid fed,
wherein a pressure detector is provided in the feeding duct and connected with the controller, or
wherein a feeding bottle is provided at an end of the feeding duct for feeding an infant or an animal, and a pipe extends outward at a front of the feeding bottle and a membrane is provided in the pipe for ventilation to balance pressure inside and outside the feeding bottle, or
wherein a feeding syringe attached to the feeding duct and an infrared detector is provided on a front and a rear walls of the feeding syringe and connected with the controller to detect a position of a piston in the feeding syringe.

15. The device, as recited in claim 14, wherein the pressure detector is provided in the feeding duct and connected with the controller.

16. The device, as recited in claim 14, wherein the feeding bottle is provided at the end of the feeding duct, and the pipe extends outward at the front of the feeding bottle and the membrane is provided in the pipe for ventilation to balance pressure inside and outside the feeding bottle.

17. The device, as recited in claim 14, wherein the feeding syringe attached to the feeding duct and the infrared detector is provided on the front and the rear walls of the feeding syringe and connected with the controller to detect the position of the piston in the feeding syringe.

18. The device, as recited in claim 17, wherein an ultrasonic detector is provided on a syringe adaptor connected to the feeding syringe to detect the position of the piston.

19. An automatic feeding device, comprising:
a controller;
a liquid food supply device;
a pump connected with the controller;
a feeding duct connected with the pump and configured to be inserted into a stomach of a patient through a nose or directly into the stomach; and
a camera, which is connected to the controller via a wire or wirelessly, to detect a feeding process.

* * * * *